United States Patent [19]

Poncy et al.

[11] 4,027,673
[45] June 7, 1977

[54] DIGITALLY INSERTABLE TAMPON

[76] Inventors: Mark P. Poncy; Richard P. Poncy; George W. Poncy, all of 3660 E. Indus. Way, Riviera Beach, Fla. 33404

[22] Filed: Sept. 29, 1975

[21] Appl. No.: 617,497

[52] U.S. Cl. .............................. 128/285; 128/270
[51] Int. Cl.² ........................................ A61F 13/20
[58] Field of Search .......... 128/270, 285, 290, 271, 128/263

[56] References Cited

UNITED STATES PATENTS

| 393,546 | 11/1888 | Dayan | 128/270 |
|---|---|---|---|
| 1,634,555 | 7/1927 | Peloubet | 128/285 |
| 1,915,794 | 6/1933 | Leonhardt | 128/270 |
| 2,301,868 | 11/1942 | Gurley, Jr. et al. | 128/270 X |
| 2,676,594 | 4/1954 | Milcent | 128/285 |
| 2,884,925 | 5/1959 | Meynier, Jr. | 128/270 |
| 2,922,422 | 1/1960 | Bletzinger | 128/263 |
| 2,922,423 | 1/1960 | Rickard et al. | 128/263 |
| 3,358,686 | 12/1967 | Kunitamiaska | 128/263 |
| 3,491,758 | 1/1970 | Mullan | 128/285 |
| 3,559,646 | 2/1971 | Mullan | 128/270 |
| 3,674,029 | 7/1972 | Bates | 128/285 |
| 3,749,094 | 7/1973 | Duncan | 128/285 |
| 3,794,024 | 2/1974 | Kokx et al. | 128/285 |
| 3,794,029 | 2/1974 | Dulle | 128/285 |
| 3,881,485 | 5/1975 | Davis, Jr. | 128/270 |

*Primary Examiner*—Aldrich F. Medbery
*Attorney, Agent, or Firm*—Lane, Aitken, Dunner & Ziems

[57] ABSTRACT

In a tampon comprising an absorptive relatively non-compressible core surrounded by a transmissive foam jacket, the foam jacket is formed into a skirt extending from the lower end of the core to define an opening to receive the finger of the user for digital insertion.

9 Claims, 3 Drawing Figures

DIGITALLY INSERTABLE TAMPON

BACKGROUND OF THE INVENTION

This invention relates to intravaginal catamenial tampons and more particularly, it concerns improvements in intravaginal catamenial tampons of the digitally inserted type.

Intravaginal tampons are in common use by women for the retention of fluids or menses discharged along the walls of the vagina during the menstrual cycle. Such tampons are usually formed of absorbent materials such as cotton, rayon cellulose wading, synthetic sponge, cellulose fluff, synthetic fibers or combinations of these materials and compressed or molded usually to a generally cylindrical configuration of a size to fit within the vaginal tract.

Several problems are associated with the use of intravaginal tampons for the collection and retention of menstrual fluids. For example, the peripheral interior contour of the vaginal wall, being unpredictably irregular as compared with the preformed tampon often leads to the by-pass of fluid menses through the occasional spaces encountered between the outer surface of the tampon and the inner vaginal wall. If the tampon itself is sufficiently flexible or compressible to conform with the peripheral configuration of the vaginal tract, the compressibility of the tampon itself reduces the effectiveness of the tampon to retain or store the menstrual fluids. In particular, compression of the tampon will result in the discharge of accumulated fluids both when the tampon is compressed directly such as during withdrawal or indirectly due to the increase in intravaginal pressure caused by the most common of body movements.

Because of the configuration of the vaginal tract and nature of menstrual fluid flow, conventional fibrous tampons fall short of full utilization of saturation capacity. Specifically, the menstrual fluids flow down along the walls of the vagina and tend to be collected at the frontal end of the tampon whereas the major absorptive surface exposure is along the sides of the tampon adjacent the vaginal walls. At this area however, the direction of fluid flow is perpendicular to the tampon surface and thus less than ideal for full absorption into the tampon. Finally, and perhaps because of the aforementioned difficulties, the use of tampons is commonly accompanied with undesirable irritation as a result of frequent insertion and withdrawal during periods of heavy menses flow. Also chafing may occur during periods of light menses flow because of the tendency of the tampon to absorb whatever small amount of liquids are present on the vaginal walls thereby to generate excess friction between the tampon and the vaginal walls.

The above described difficulties experienced with intravaginal catamenial tampons are substantially alleviated by the invention described in the copending application Ser. No. 587,677, filed June 17, 1975, invented by Richard P. Poncy, Mark P. Poncy, George W. Poncy, Sr., George W. Poncy, Jr. and Robert C. Brandriff, entitled "Catamenial Tampon Having Fluid Transmissive and Resilient Outer Sheath." In the tampon described this copending application, a conventional noncompressible fibrous tampon is enclosed in a compressible, open-celled or reticulated hydrophilic foam which transfers by capillary action munstrual fluids from the vaginal wall to the fibrous material which in the overall tampon of the invention is in the nature of a non-compressible core. The compressibility of the exterior foam layer allows the tampon to be easily inserted and also to maintain a constant yet gentle pressure about the interior of the vaginal walls. Moreover, because the foam is pocketed with enumerable openings or pores on the surface thereof in contact with the vaginal wall, a full transfer of fluid from the vaginal wall to the formed surface is assured. Because the inner absorbent core maintains a greater affinity for fluid thanthe non-absorbent vaginal walls surrounding the entire tampon, the direction of capillary action through the open-celled hydrophilic foam is toward the core. This factor is particularly significant during periods of strenuous muscular activity which would lead to the compression of the foam envelope or outer layer. In other words, the direction of capillary action is such that upon compression of the foam, the fluid is discharged to the core as distinguished from outwardly of the foam.

The tampon of the present invention is an improvement over the tampon described in the above mentioned copending application and employs the same general construction of a relatively noncompressible absorptive core enclosed in a jacket of an elastomeric foam, which is of the type designed to transmit fluids by capillary action rather than store fluids. Thus, the tampon of the present invention has the same advantages of increased effective capacity, which is substantially unaffected by compression, and of providing greater comfort to the user as the tampon described in the above mentioned copending application.

The tampon of the above described copending application is inserted in a conventional manner by means of an applicator. The tampon of the present invention differs from the tampon described above in that it is designed for digital insertion rather than by an applicator. While digitally inserted tampons are quite popular in Europe because they eliminate the need for and expense of an applicator, they have never been well received in this country apparently because the digital insertion technique required is awkward and results in the user soiling her hands. The improved tampon design of the present invention permits it to be inserted very easily and without soiling the fingers or hands of the user.

In accordance with the present invention, the bottom of the foam jacket which encloses the absorptive core extends below the absorptive core as a cylindrical skirt which is open to the absorptive core so that the user's finger may be inserted into the skirt in contact with the noncompressible core. With the user's finger inserted within the skirt against the core, the core with the foam jacket acts like an extension of the user's finger keeping alignment therewith as the inserted finger is manipulated thus greatly facilitating insertion into the vagina. Because the finger is covered by the foam skirt, the digital insertion can be easily carried out without soiling the finger of the user.

The foam skirt is provided with rings extending around and through the skirt, in which rings the foam cells are closed so as to provide a barrier from menstrual fluids being drawn down through the foam skirt. While there is no bonding of the core to the foam jacket surrounding it, a string embedded in the core can readily withdraw the core with the foam jacket because any tendency of the core to be pulled outof the jacket will cause the jacket to constrict more tightly around the core. Alternatively, the withdrawal string may be dispensed with and the foam skirt used to withdraw the tampon.

Further objects and advantages of the present invention will become readily apparent as the following detailed description of the invention unfolds when taken in conjunction with the drawings identified below.

DESCRIPTION OF A PREFERRED EMBODIMENT

Figure 1:
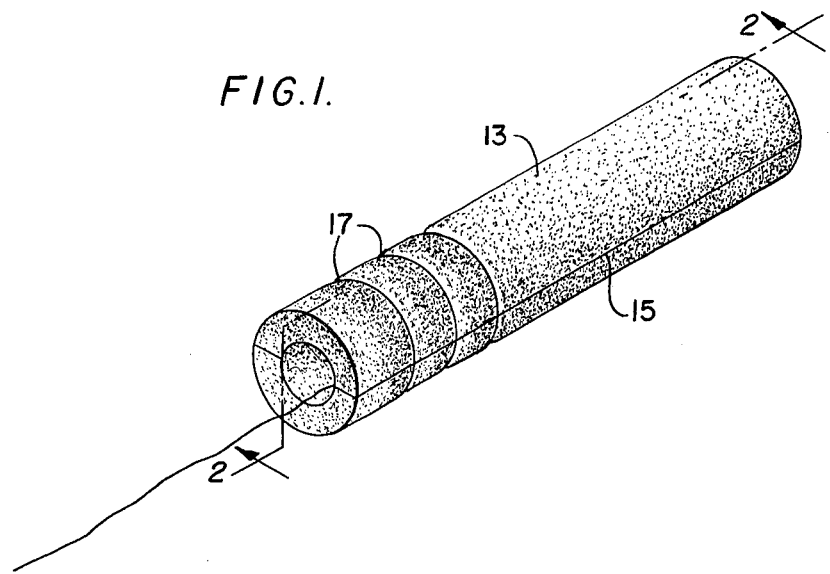
FIG. 1 is a perspective view of the tampon of the present invention.
Figure 2:
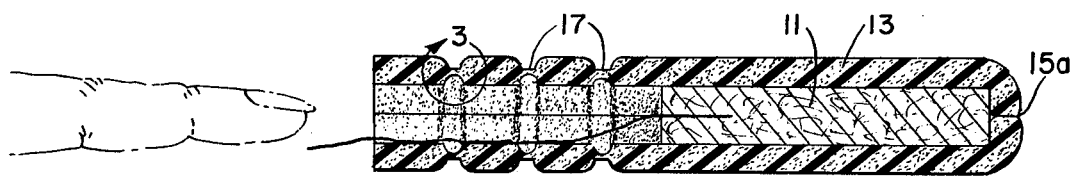
FIG. 2 is a sectional view taken along the lines 2—2 of FIG. 1 and illustrating how the user's finger is inserted into the skirt of the tampon.
Figure 3:
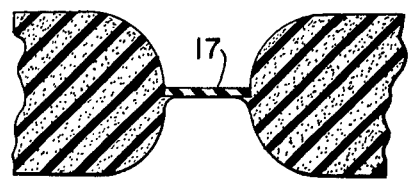
FIG. 3 is an enlarged sectional view of the area in the circle 3.

As shown in FIG. 1, the improved tampon of the present invention is of a generally cylindrical configuration and comprises a generally cylindrical absorptive core 11 of relatively noncompressible absorbent fibrous material surrounded by a jacket 13 made of elastomeric open-celled foam. The jacket 13 does not enclose the core at the bottom thereof, but extends below it in a cylindrical skirt. The foam jacket 13, as best illustrated in FIG. 2, extends over and covers the upper end of the tampon. The jacket is made from two sheets of the foam material which are wrapped around the core 11 with the core sandwiched between the two sheets and the edges of the sheets are heat-sealed together in a slightly stretched condition to form a seam 15 in the foam jacket. A portion of each of the sheets of foam is allowed to lap over the upper end of the core and these portions of the sheets are folded over the end of the core and are also sealed together as a continuation 15a of the seam 15 over the end of the core 11 to completely enclose the upper end of the core 11 within the jacket 13. The material of the skirt is formed into three non-porous bands 17 extending all the way around the skirt and extending substantially through the entire width of the skirt. These non-porous bands are formed by applying heat and pressure through the thickness of the material in order to melt the material into a solid elastomeric band of material. The non-porous bands 17 may be formed conventionally by forming non-porous lines in the foam sheets before they are wrapped around the core 11 to form the jacket 13 by means of a hot roller or by a hot die. These non-porous bands serve to prevent menstrual fluid from being drawn by capillary action down the skirt of the device.

In the preferred embodiment, the core 11 is formed from a conventional junior sized tampon such as those available commercially under the trademark "Pursette" or "Carefree." The construction of the core may be the same as that of the tampon disclosed in U.S. Pat. No. 2,440,141 to Donovan, in U.S. Pat. No. 2,808,832 to Myers et al, or in U. S. Pat. No. 2,553,000 to Parish.

The overall length of the device is about 4½ inches and the skirt has a length of about 2 inches. The foam jacket has a wall thickness of about ¼ inches. The core is about ⅝ inches in diameter so the overall diameter for the device is about ⅞ inches.

In the embodiment shown in the drawings, a removal string 19 is embedded in the core 11 and extends out through the skirt. The device can be withdrawn after use by means of the string even though the core is not bonded in any way to the foam jacket because any tendency of the core 11 to move with respect to the jacket when the string is pulled will cause the jacket to constrict more tightly around the core and thus oppose any such movement in a manner similar to the action of a Chinese finger grip. Alternatively, the string can be eliminated and the skirt used to withdraw the device.

The material of the foam as in the above identified copending application is formed from reticulated polyurathane having in excess of 60 pores per linear inch and preferably about 80 pores per linear inch. A complete disclosure of this foam and its method of manufacture is found in U.S. Pat. No. 3,171,820 issued Mar. 2, 1965 to Robert A. Voltz and U.S. Pat. No. 3,175,025 issued Mar. 23, 1965, which patents are hereby incorporated by reference. As disclosed in these patents, reticulated foam is foam having a structure in the nature of an open skeletal network of linear interconnecting elements. The material of the reticulated foam is made hydrophilic by means of appropriate wetting agents.

Reticulated foam is selected for the jacket 13 for the same reasons it is used in the tampons of the above identified copending application. The purpose of the jacket 13 is to transmit the menstrual fluid to the core 11 rather than store it and the object is for as little of the fluid to be stored in the jacket as possible. Because reticulated foam transmits fluids very efficiently and it is transmitting to a highly absorptive core, very little fluid is stored in the foam jacket. On the other hand, the core 11 stores more fluid than does a conventional tampon even though the core is the same as a conventional tampon because the soft resilient foam making close contour following contact with the vagina walls more efficiently collects the menstrual fluid from the vagina walls and transfers it to the core.

To insert the tampon, the user merely inserts her finger fully into the foam skirt to engage the bottom end of the core 11 and then with the tampon on the finger digitally inserts the tampon into the vagina. The opening in the skirt is sized so that it fits snugly around the human finger in a slightly stretched condition. Because the finger engages the core directly, the device acts like an extension of the finger with the tampon maintaining axial alignment with the finger and is easy to manipulate during the insertion operation. Because the finger is surrounded by the foam skirt, the operation can be carried out without the finger coming into contact with the menstrual fluid and thus soiling of the finger is prevented.

While the above described digitally inserted tampon has been described as employing transmissive foam, such as reticulated foam, it is clear that the principal of the skirt protection is applicable to other types of tampons. For example, the foam skirt could be employed in connection with the tampon disclosed in the co-pending application Ser. No. 587,676, filed June 17, 1975, invented by Richard P. Poncy, Mark P. Poncy, George W. Poncy, Sr., George W. Poncy, Jr., and Robert C. Brandriff, entitled "Catamenial Tampon." In the tampon described in this application, the foam jacket is made from closed-cell foam rather than opened-cell foam and requires that the upper end of the core be open rather than closed. In addition, the principal of the skirt can be employed in tampons not employing foam jackets at all. For example, an impervious, elastomeric skirt could be provided on a conventional tampon. These and many other modifications may be made to the above described preferred embodiment of the invention departing from the spirit and scope of the invention, which is defined in the appended claims.

We claim:

1. A digitally insertable tampon comprising a generally cylindrically shaped member made of material adapted to absorb and store menstrual fluid being of a size and shape to function as a catamenial tampon, a cylindrical skirt attached to said cylinder extending from one end thereof to define an opening axially aligned with said cylinder, said opening being of a size and shape so that said skirt fits snugly around and surrounds a substantial portion of a human finger inserted fully into said opening and means for preventing menstral fluid from coming in contact with the inserted finger when the tampon in digitally inserted into the vagina comprising said skirt opening being of a sufficient depth for said skirt to cover a sufficient portion of said finger to avoid menstrual contact.

2. A tampon as recited in claim 1, wherein said skirt is made of elastomeric material and is of a size so that it can be stretched to fit snugly around the finger of the user in a stretched condition.

3. A tampon as recited in claim 1, wherein said cylindrically shaped member comprises an absorptive core surrounded by a resilient foam jacket, said skirt being an extension of said jacket from one end of said core.

4. A tampon as recited in claim 3, wherein said jacket is made of open-celled transmissive foam which will transmit menstrual fluid by capillary action.

5. A tampon as recited in claim 4, wherein said foam is reticulated foam.

6. A tampon as recited in claim 4, wherein said skirt has at least one band defined therein extending around said skirt and substantially through said skirt, the material of said band being non-porous.

7. A tampon as recited in claim 1, wherein said cylindrically shaped member comprises a cylindrical core of substantially noncompressible absorptive material and wherein the opening defined by said skirt extends to said core and is of a sufficient size throughout its length so that a finger inserted into said opening can be brought into contact with said core.

8. A tampon as recited in claim 1, wherein said skirt with said opening comprises means to maintain axial alignment of the tampon with a finger inserted into said opening.

9. A tampon as recited in claim 1, wherein the depth of said opening is in excess of the diameter of said opening.

* * * * *

UNITED STATES PATENT OFFICE
CERTIFICATE OF CORRECTION

Patent No. 4,027,673          Dated June 7, 1977

Inventor(s) Mark P. Poncy et al

It is certified that error appears in the above-identified patent and that said Letters Patent are hereby corrected as shown below:

Claim 1, line 16, "in" should be changed to --is--.

Signed and Sealed this sixteenth Day of August 1977

[SEAL]

Attest:

RUTH C. MASON
*Attesting Officer*

C. MARSHALL DANN
*Commissioner of Patents and Trademarks*